US011885135B2

(12) United States Patent
Amendolea (10) Patent No.: US 11,885,135 B2
(45) Date of Patent: Jan. 30, 2024

(54) UNIVERSAL GRAB BAR WITH ONE PIECE MOLDED MOUNT AND INTEGRATED ACCESSORIES

(71) Applicant: Rick Amendolea, Columbiana, PA (US)

(72) Inventor: Rick Amendolea, Columbiana, PA (US)

( * ) Notice: Subject to any disclaimer, the term of this patent is extended or adjusted under 35 U.S.C. 154(b) by 529 days.

(21) Appl. No.: 17/178,069

(22) Filed: Feb. 17, 2021

(65) Prior Publication Data

US 2021/0172177 A1 Jun. 10, 2021

Related U.S. Application Data

(63) Continuation of application No. 15/046,898, filed on Feb. 18, 2016, now abandoned.

(60) Provisional application No. 62/137,497, filed on Mar. 24, 2015, provisional application No. 62/117,925, filed on Feb. 18, 2015.

(51) Int. Cl.
| | |
|---|---|
| *E04F 11/18* | (2006.01) |
| *H04R 1/02* | (2006.01) |
| *A61L 9/03* | (2006.01) |
| *A61L 9/12* | (2006.01) |
| *A47K 5/12* | (2006.01) |

(52) U.S. Cl.
CPC .......... *E04F 11/1804* (2013.01); *H04R 1/028* (2013.01); *A47K 5/12* (2013.01); *A61L 9/03* (2013.01); *A61L 9/12* (2013.01); *H04R 2420/07* (2013.01)

(58) Field of Classification Search
CPC ....... A61L 9/03; A47K 2201/02; A47K 3/003; A47K 17/022; A47H 1/102; A47H 1/142; E04F 11/1804; F21V 23/04; F21V 23/009; F21V 33/004; F21V 33/006
See application file for complete search history.

(56) References Cited

U.S. PATENT DOCUMENTS

| | | | |
|---|---|---|---|
| 2,807,834 A | 10/1957 | Blum | |
| 2,886,278 A | 5/1959 | Opie | |
| 3,164,354 A * | 1/1965 | Murdock | ............ E04F 11/1804 256/65.03 |
| 3,223,371 A | 12/1965 | Miller | |
| 3,306,641 A | 2/1967 | Blum | |
| 3,343,811 A | 9/1967 | Kusel et al. | |
| 3,433,360 A | 3/1969 | Duchek et al. | |
| 3,569,689 A * | 3/1971 | Nestrock | ............... F21V 33/006 362/146 |

(Continued)

*Primary Examiner* — Daniel J Wiley
(74) *Attorney, Agent, or Firm* — Blynn L. Shideler; Krisanne Shideler; BLK Law Group (57) ABSTRACT

A rapidly mounted, modular, universal handrail and grab bar system is disclosed having a plurality of one piece molded wall mounted supports; a plurality of fasteners securing the wall supports, wherein each support is initially rotationally adjustable about the fastener; at least one stock rail member forms the handrail member, wherein each rail member is received within wall support rail recesses, and wherein the central fastener extends perpendicular to the axis of the rail member; and at least one lateral fastening member to secure the rail member to the support. The rail members can include integrated accessories such as lighting units, glow in the dark elements, speakers, radio, scent releasing units, and liquid/powder dispensers.

20 Claims, 4 Drawing Sheets

(56) References Cited

U.S. PATENT DOCUMENTS

| | | | | |
|---|---|---|---|---|
| 3,633,862 A * | 1/1972 | Breen | | F16B 9/052 |
| | | | | 256/65.16 |
| 4,398,691 A * | 8/1983 | Wilke | | A47K 10/10 |
| | | | | 248/235 |
| 4,650,164 A | 3/1987 | Shepherd | | |
| 4,895,332 A * | 1/1990 | Hansen | | A47K 3/003 |
| | | | | 248/251 |
| 5,050,252 A * | 9/1991 | Cuttriss | | A47K 17/022 |
| | | | | 4/576.1 |
| 5,284,444 A * | 2/1994 | Raynes | | G09B 21/007 |
| | | | | 116/DIG. 17 |
| 5,450,299 A * | 9/1995 | Lepre | | E04F 11/1804 |
| | | | | 362/276 |
| 6,270,058 B1 | 8/2001 | Williams et al. | | |
| 6,371,423 B1 * | 4/2002 | Miller | | A47H 1/102 |
| | | | | 248/221.12 |
| 6,508,458 B1 | 1/2003 | Bartlett et al. | | |
| 6,553,629 B2 * | 4/2003 | Grady | | B60Q 3/267 |
| | | | | 362/399 |
| 7,934,701 B2 * | 5/2011 | Kay | | B21C 23/142 |
| | | | | 256/1 |
| 8,070,137 B2 * | 12/2011 | Bennett | | A47K 17/022 |
| | | | | 256/65.16 |
| 8,382,051 B2 * | 2/2013 | Smith | | A47K 10/10 |
| | | | | 248/221.11 |
| 9,181,709 B2 | 11/2015 | Amendolea | | |
| 11,428,401 B2 * | 8/2022 | Edwards | | A47K 10/38 |
| 2007/0086852 A1 * | 4/2007 | Goad | | E04F 11/1808 |
| | | | | 403/292 |
| 2008/0018437 A1 * | 1/2008 | Reichling | | B60R 25/1001 |
| | | | | 340/426.1 |
| 2008/0080173 A1 * | 4/2008 | Trimble | | E04F 11/18 |
| | | | | 362/146 |
| 2008/0184475 A1 * | 8/2008 | Sladick | | G02B 6/0008 |
| | | | | 362/147 |
| 2009/0205123 A1 * | 8/2009 | Forrest | | A47K 17/022 |
| | | | | 4/576.1 |
| 2009/0206220 A1 * | 8/2009 | Forrest | | A47K 3/003 |
| | | | | 248/251 |
| 2009/0211014 A1 * | 8/2009 | Forrest | | A47K 17/022 |
| | | | | 248/251 |
| 2011/0248134 A1 * | 10/2011 | Goad | | A47K 17/022 |
| | | | | 248/224.7 |
| 2013/0167454 A1 | 7/2013 | Amendolea | | |

\* cited by examiner

UNIVERSAL GRAB BAR WITH ONE PIECE MOLDED MOUNT AND INTEGRATED ACCESSORIES

RELATED APPLICATIONS

This application claims the benefit of application Ser. No. 15/046,898 filed Feb. 18, 2016, which application is incorporated herein by reference.

application Ser. No. 15/046,898 claims priority to U.S. patent application Ser. No. 62/117,925 filed Feb. 18, 2015, entitled "Universal Grab Bar with One Piece Molded Mount with Integrated Accessories."

application Ser. No. 15/046,898 claims priority to U.S. patent application Ser. No. 62/137,497 filed Mar. 24, 2015, entitled "Universal Grab Bar with One Piece Molded Mount with Integrated Accessories."

BACKGROUND INFORMATION

1. Field of the Invention

The present invention relates to grab bars, and more particular to a rapidly mounted, modular, universal grab bar with one piece molded mount with integrated accessories.

2. Background Information

A handrail is a rail that is designed to be grasped by the hand so as to provide stability or support. Handrails are commonly used while ascending or descending stairways in order to prevent injurious falls. They can also be called banisters and balustrades. Handrails are typically supported by posts (or balusters) or mounted directly to walls. Other common handrail applications include handrails surrounding balconies.

A further common handrail application is forming a barre (also called a bar), which serve as training aids for ballet dancers. A barre is a stationary handrail that is used during ballet warm up exercises. The term also refers to the exercises that are performed at the barre, as well as that part of a ballet class that incorporates barre exercises.

A further common subset of handrails is known as grab bars. A grab bar is commonly identified as a bar forming a handhold which is designed to help people with disabilities. Grab bars are commonly found in accessible restrooms where they help people get in and out of wheelchairs and walkers. Grab bars can also be installed in full bathrooms to help people navigate the bathroom. In some homes, grab bars are installed in many locations around the house, anticipating a variety of potential needs. Although there is no precise limit or defining length, a grab bar is generally a shorter type hand rail. In fact in most applications a grab bar is a hand rail having only two supports.

There are a number of hand rail and grab bar systems illustrated in the prior art. For example U.S. Pat. No. 6,932,328 assigned to Constructions Specialties, Inc. discloses a rail and wall support installation includes an adapter which mechanically couples a wall support having a rotatable locking cam portion to an undercut groove on the rear of the rail. The adapter serves both as a mechanical attachment point for the rail to a wall support and to transfer the cam action of the locking cam portion to the rail. U.S. Pat. Nos. 6,508,458 and 6,270,058 also assigned to Constructions Specialties, Inc. discloses a similar systems.

U.S. Pat. No. 4,650,164 describes handrail system for suspending a handrail spaced from a supporting structure such as a wall with internal clamping brackets providing a trim appearance. The handrail system includes an elongated generally cylindrical rail body having a tubular wall of generally uniform wall thickness surrounding a hollow interior region. Slots are formed in the tubular wall along a line parallel with the rail axis. A rail support assembly connects each slot to the supporting structure. Each rail support structure includes a pair of similar stamped and formed metal brackets. Each bracket includes a flat body and an arm of reduced size extending from the body at an angle and defining a pair of rail engaging shoulders on the body. The arms are inserted through a slot into generally side-by-side relation within the hollow interior region with the shoulders extending beyond the slots. A threaded fastener engages the support structure and the brackets for clamping the bodies together and separating the arms to clamp the interior of the rail and hold the rail against the shoulders.

U.S. Pat. Nos. 3,433,360 and 3,343,811 disclose handrail mounting systems. Other relevant teachings can be found in U.S. Pat. Nos. 3,306,641, 3,223,371, 2,886,278, and 2,807,834.

Many currently available commercial grab bar products are configured with a flange mount that typically utilizes a two or three bolt-mounting pattern. When vertically mounted, these patterns provide for typically only one fastener, at best, on each end to align with a wall stud. If horizontally mounted, engaging a stud with a fastener is only possible if the length of the grab bar is such that it agrees with the spacing of the wall studs, and more often than not, the spacing does not agree. When anchoring to a wall stud is not possible, current grab bar manufacturers recommend using special fasteners such as a Wingits™ brand specialty fasteners and similar fasteners, or toggle bolts or the like. Wingits™ are very expensive and labor intensive. Toggle bolts are not as strong as anchoring to a stud. Consequently wall anchoring of the supports to a stud is preferred.

Thus, for optimum mounting strength, the length of the grab bar must match the spacing of the wall studs so that a fastener can be secured directly to a wall stud. Current commercial grab bar lengths are not adjustable or selectable. As noted above, many if not most of the available grab bar lengths do not agree with stud spacing. Installation is more involved, more time consuming, more labor intensive and more expensive when using special fasteners such as Wingits™ type fasteners, which are necessary when, anchoring to a wall stud is not possible.

Despite the plethora of handrail and grab bar systems developed there remains a need for a cost effective rapidly mounted, modular, universal grab bar and handrail system. There is a need for an easy and cost effective rapidly mounted, modular, universal grab bar and handrail system and easy back to back grab bar mounting.

The inventors have addressed some of these deficiencies of the prior art with the rapidly mounted, modular, Universal Grab Bar and Handrail System set forth in U.S. Pat. No. 9,181,709, which issued Nov. 10, 2015 and which published as U.S. Publication Number 2013-0167454, which patent and publication is incorporated herein by reference. The present invention is directed to improvements in the design of the type of grab bar disclosed in the '709 patent to improve the economic advantage and commercial applicability of the design.

SUMMARY OF THE INVENTION

One embodiment of this invention is directed to a rapidly mounted, modular, universal grab bar system. The system comprises: a rail member and a plurality of wall mounted supports, wherein each wall mounted support is formed as a one piece molded member having a wall end configured to be adjacent the wall with a central fastener opening extending from the wall end through to a distal end and wherein the one piece molded member forming the wall mounted support includes a rail member recess formed as a through-hole extending from one side of the wall mounted support through to an opposed side of the wall mounted support and intersecting with the central fastener opening and wherein each wall mounted support is configured to be secured to a wall, and wherein the central fastener opening is formed as a first bore extending from the wall end to an enlarged head receiving portion having a diameter larger than a diameter of the first bore extending to the distal end, wherein the enlarged head receiving portion is accessible through the distal end of the wall support and wherein the intersection of the enlarged head receiving portion with the first bore is at least one half of the distance of from the wall end to the through-hole forming the rail member recess; a plurality of central fasteners, each central fastener with a drive head and associated with at least one wall mounted support and received within the central fastener opening thereof for securing each wall mounted support to the wall through the central fastener, wherein the central fastener is configured to be accessed through the distal end of the wall mounted support, wherein the wall mounted support is, at least at one time, rotationally adjustable about the central fastener, and wherein the one piece wall mounted support is substantially solid surrounding the central fastener opening from the one end to the through-hole forming the rail member recess; and at least one stock rail member forming the handrail member, wherein each rail member is received within rail member recesses of the wall mounted supports extending entirely through the through-hole forming the rail member recess and wherein the central fastener extends perpendicular to the axis of the rail member, wherein the rail member recess of each wall mounted support being formed as a through-hole whereby the recess substantially encircles the rail member which is received within rail member recess and aligns the rail member which is received within rail member recess with the associated central fastener which is received within the central fastener opening.

Another aspect of the present invention provide a rapidly mounted, modular, universal grab bar system having a plurality of one piece molded wall mounted supports; a plurality of fasteners securing the wall supports, wherein each support is initially rotationally adjustable about the fastener; at least one stock rail member forms the handrail member, wherein each rail member is received within wall support rail recesses, and wherein the central fastener extends perpendicular to the axis of the rail member; and at least one lateral fastening member to secure the rail member to the support. The rail members can form a pair of back to back mounted grab bars on opposed sides of a partition, wherein a plurality of the wall mounted supports are on each side of the partition.

A further aspect of the present invention is providing a rapidly mounted, modular, universal grab bar system having an integrated accessory such as an accessory including one or more of the following functionalities: a Glow in the Dark grab bar; a Lighted grab bar; a Wireless speaker grab bar; a Radio grab bar; a Scent emitting grab bar; a Heated grab bar; and a Vibrating grab bar. Where appropriate the following grab bar accessory can be actuated (switching on-off) by a number of different sensing technologies, such as Motion-detecting (ultrasonic and microwave), Heat-sensing (infrared), Sound-sensing (acoustic), Touch sensing (capacitance and resistive), a Light sensing (photocell), and a Passive infrared sensing (occupancy). Mechanical switches can also be employed.

It is noted that, as used in this specification and the appended claims, the singular forms "a," "an," and "the" include plural referents unless expressly and unequivocally limited to one referent.

The features that characterize the present invention are pointed out with particularity in the claims which are part of this disclosure. These and other features of the invention, its operating advantages and the specific objects obtained by its use will be more fully understood from the following detailed description and the operating examples.

BRIEF DESCRIPTION OF THE FIGURES

The invention is illustrated by way of example, and not by way of limitation in the figures of the accompanying drawings.

FIGS. 1 and 4A and B are perspective views of a typical grab bar assembly according to the present invention;

FIGS. 2B and C are bottom and top plan views, respectively, of the one piece molded mount for the grab bar assembly of FIG. 1;

DESCRIPTION OF THE PREFERRED EMBODIMENTS

The present invention can easily be described in connection with the front mounted, modular, universal grab bar system 10 shown in the figures that may be mounted to a wall on studs. Further discussion on the mounting of this type of system is found in in U.S. Pat. No. 9,181,709 entitled "Universal Grab Bar and Handrail System" and which published as U.S. Publication Number 2013-0167454, which patent and publication is incorporated herein by reference. The system 10 includes a plurality of one piece molded mounts or wall supports 20 shown in greater detail in FIGS. 2A-F and 3. Each wall mount 20 can be easily molded of plastic, or other material of suitable strength, and can include any ornamental outer configuration and finish as desired. The cored circular cross section shown for the mounts 20 is believed to be the easiest from a manufacturing standpoint. Each wall mounted support 20 includes a rail member recess 26 or through hole extending generally perpendicular to a longitudinal axis of the mount 20. The rail member recess 26 is in the form of a rail member encircling through-hole opening and is aligned with a central fastener opening 36 that extends generally along the longitudinal axis of the mount 20. The central fastener opening 36 is stepped to allow for receipt and rotation of the head of a central faster 24.

In general, each wall support or mount 20 is secured to a wall stud with a fastener 24, wherein each central fastener 20 includes a drive head and is associated with a wall mounted support or mount 20 for securing each mount 20 to the wall through the central fastener 24. The central fastener 24 may be any number of conventional fasteners, such as a steel fastener with a hex or Allen head drive head and a wood engaging end for use with the wood studs of the walls. Each molded mount 20 is, at least at time of initial wall attachment, rotationally adjustable about the central fastener 24 to allow for proper alignment with other laterally spaced wall supports 24 of the system or assembly 10.

The grab bar system 10 includes at least one stock rail member 12 forming the grab bar. The rail member 12 may be interchangeably referenced as a grab bar 12, rail 12, bar 12 or similar term herein. Each rail member 12 is received within rail member recesses 26 of the mount 20. The central fastener 24 of each wall support 20 extends perpendicular to the axis of the rail member 12. The stock rail member 12 can be easily formed of common metal bar stock 12 (or plastic stock) which can be easily cut to length by the user for a designated length. The rail member 12 can have numerous decorative finishes as desired (such as a knurled surface for improved grip) and the material selection is dependent only upon the strength requirements for the grab bar 12. For example, plastic may be utilized for certain implementations of the rail 12, such as the glow in the dark application. The rail member 12 is shown used with two mounts 20, but three or more mounts 20 could be implemented with a single section or piece of rail member 12.

Molded, rail member end caps 14 can be used at distal ends of the grab bar rail member 12. The molded end caps 14 can take a variety of decorative shapes and be designed for accessories as discussed below in connection with FIGS. 7-11. The mounts 20 include set screw holes 30 for receipt of set screws there through to engage with the hand rail member 12 to rotationally and axially secure the hand rail member 12 in position. The pair of set screw holes 30 are positioned in the front of the mount 20 for ease of assembly and to have the set screw be covered by the molded central fastener end cap 22. Screws need not be in each opening 30 or even at each mount 20, as one screw per mount 20 or even per rail member 12 may be sufficient.

The molded one piece central fastener end cap 22 is provided for sealing the central opening 30 of the wall supports or mounts 20. The end cap 22 may include an annular array of fingers with locking projections that engage an associated undercut in the molded wall support 20. The cap 22 design having a secure snap fit coupling or other connections could be implemented. The cap 22 covers the fastener 24 and the set screws such that there are no exposed fasteners providing for a tamperproof construction that is advantageous particularly in commercial applications. The rail 12 also covers the fasteners 24, as understood.

Figure 1:
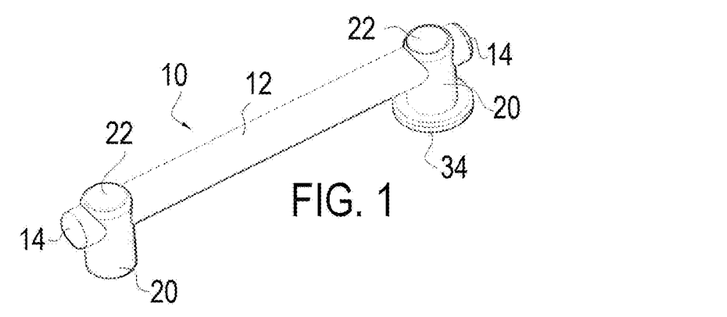
Figure 2A:
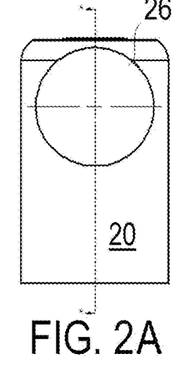
FIGS. 2A and E are side elevation views of the one piece molded mount for the grab bar assembly of FIG. 1.
Figures 2B, 4A, 4B:
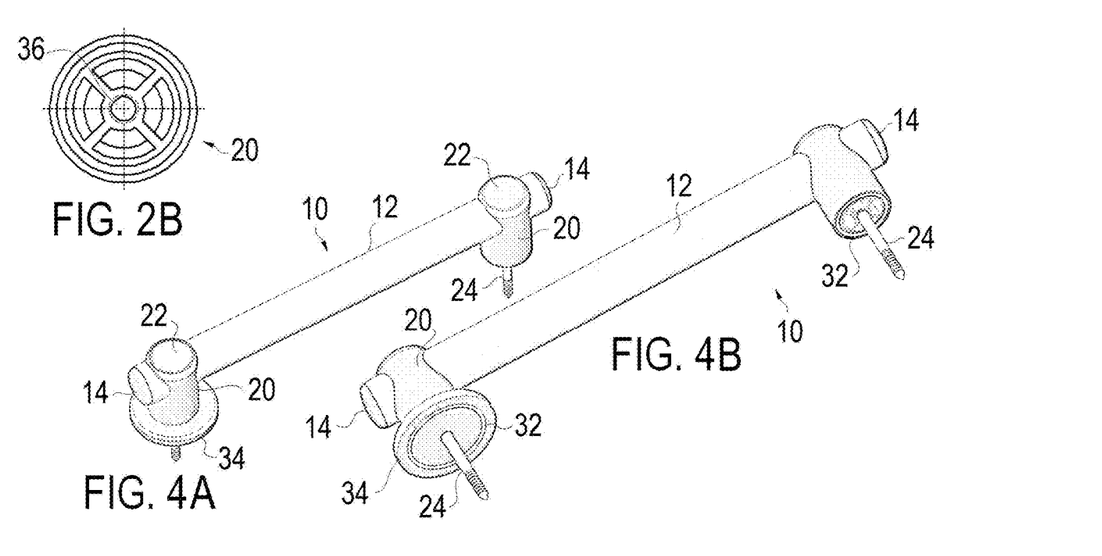
Figure 2C:
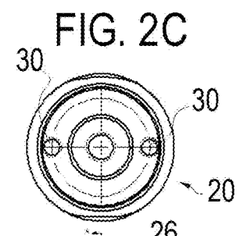
Figure 2D:
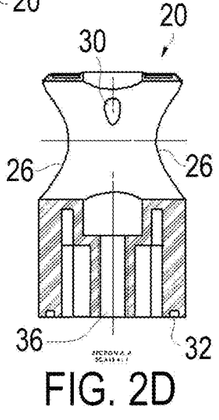
FIGS. 2D and F are side sectional views of the one piece molded mount for the grab bar assembly of FIG. 1.
Figures 2E, 2F:
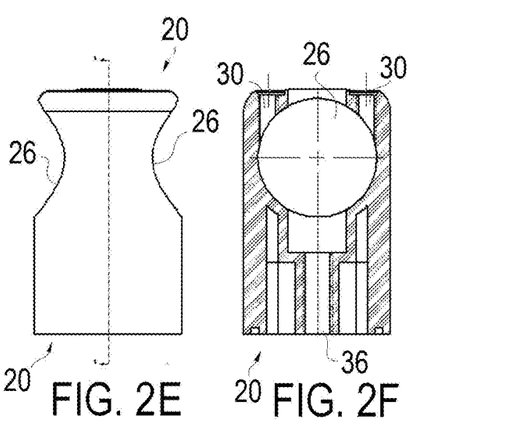
Figure 3:
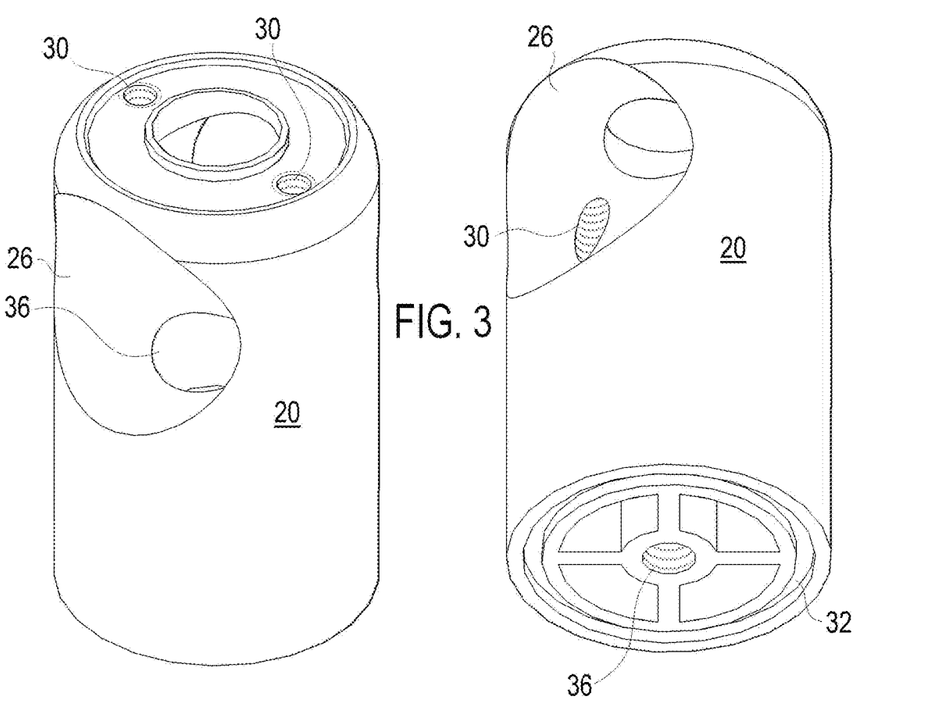
FIG. 3 is a perspective view of a pair of the one piece molded mount for the grab bar assembly of FIG. 1.
Figure 5:
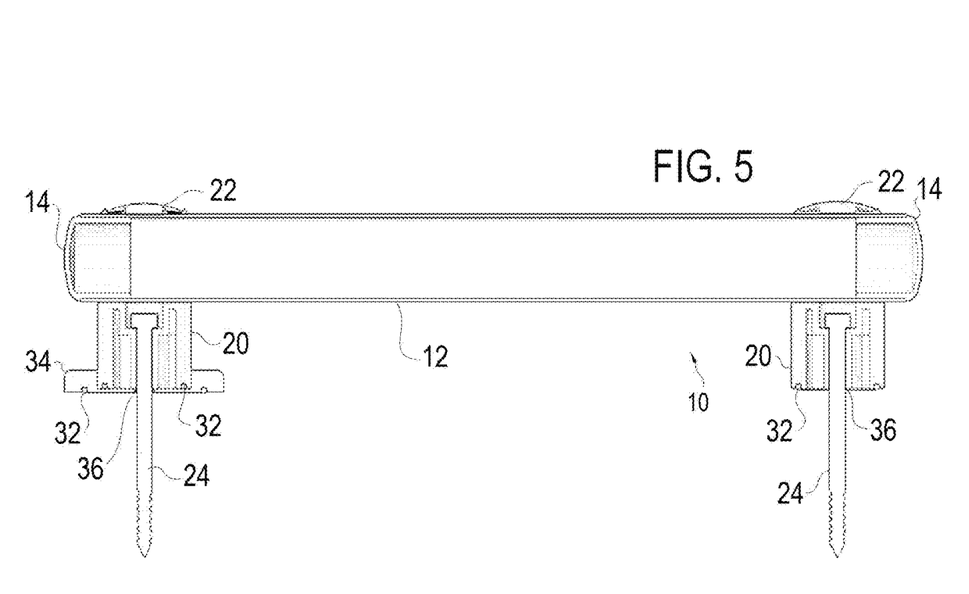
FIG. 5 is a sectional view of a typical grab bar assembly according to the present invention.

FIGS. 1 and 4A and B are included to demonstrate a typical grab bar assembly of the present invention, sold under the mark SMARTBAR™ assembly 10 of which the one piece molded mounts 20 are a key component. In its simplest form the assembly consists of the following: a bar 12; a bar cap 14 at each end of the bar 12; a pair of mounts 20, each mount with a thru hole 26 that encircles the bar 12; a pair of mount caps 22; two central fasteners 24, one fastener 24 for securing each mount 20 to a wall surface or structure; underneath each mount cap 22 are setscrews in holes 30 (although less set screws may be used than there are holes 30). Once the bar 12 is in the desired location, these setscrews secure the bar 12 from moving in the direction of the bar axis and also prevents the bar 12 from rotational movement.

FIGS. 2A-F and 3 illustrates the features of the new one piece molded mount 20 with the following characteristics: a Bar thru hole 26 which encircles the bar 12 so that bar length and the mounting distance between mounts 20 are non-critical; the mounts 20 are injection moldable; the fastener head mounting surface and the base of the mount can be sealed with O-rings in groove 32 so that the installation can be made waterproof which is highly desirable in wet or corrosive environments; single point fastening via fastener 24 through hole 36 to reduce installation complexity and labor costs; moldable from metal replacement engineered polymers. Note the cored out bottom including ribs to the material forming the central mounting srew hole 36. Features of the mount 20 include that the mount encircles the bar 12 via holes 26, allowing the bar 12 to be positioned anywhere between the mounts 12. This eliminates the necessity of precise bar length and mount 20 location such that a precise length of the bar 12 is not required and precise location of the mounting holes for mounts 20 are not required. Tamper resistance is another feature of the assembly 10 as no access to any fasteners 24 or set screws are visible due to caps 22. The single fastener 24 per mount 20 yields simple mounting. The mounts are preferably molded from reinforced thermoplastic polymer (a metal replacement engineered plastic) and the design yield a minimum number of parts required. The mounts are internally cored for material savings with ribs for strength. The coring further provides for an ease of production as the molding cycle time is greatly reduced without the core. The mount 20 material and associated hardware are highly corrosion resistant. The design includes a long engagement with the mounting fastener 24 (i.e. the head of the fastener is spaced from the wall and spaced from the end of the mount 20) for additional support and strength. The sealed mounting with O-rings in groove 32 on the mounting surface allows for sealed applications such as in bathrooms.

The system mounts 20 can be used with or without a flange 34 at the base of the mounts 20. The underside view is shown to highlight the Mount O-ring seal via O-rings in grooves 32 which is a highly reliable method of sealing without the mess and disadvantages of caulk or silicone. A similar seal may also be included on the flange 34, if used.

An effective, efficient and advantageous force transferring configuration is exhibited in the system 20 wherein the rail member recesses 26 of the wall mounted supports 20 encircle the rail member 12 and are configured to align the rail member 12 with the associated central fasteners 24. This design provides an efficient load transfer in use from the rail member 12 to the support 20 to the fastener 24 to the wall.

Further the positioning of the head of the fastener 24 more than halfway between the end of the mount 20 and the rail member recess 26, as shown, provides the structural support of the central fastener 24 to the system 10 to resist bending moments.

With front mounting, each wall support 20 is fastened with a single centralized fastener 24 from the front through the wallboard or the like and into a stud. As noted above, the wall support 24 has a rail member recess 26 in the form of a through hole, perpendicular to its axis, with a diameter sufficient for the hand rail member 12 to pass through (generally with close tolerances to avoid visible gaps). Each of the two (or more) wall supports 20 can be located on a stud regardless of the stud spacing. A fastener 24 is inserted through the front end of the fastener opening 36 of each wall support 20, and engaged into the wall and stud. Typically the fastener 24 can be driven directly into the wooden stud with no pre-drilling required. A separate conventional metal stud fastener 24 would be utilized for metal stud containing walls.

The required length of hand rail member 12 can be measured, based on the distance between the wall supports 20 and the desired overhang, and the stock material for the member 12 then cut to length. The cut member 12 is inserted through both (or more) wall supports 20 via openings 26 and secured with a set screw fastener in one or more wall supports 20 via openings 30. A predetermined length of grab bar 12 may also be used with the grab bar 12 centered within the wall secured mounts 20, as the predetermined lengths of grab bar may make it easier to include some of the integrated accessories discussed below.

The present invention provides a simple to install grab bar system 10 that can be adjusted for any length and wall stud spacing and for any desired angle. The ease of cutting the bar stock 12 to length minimized the number of components an installer must carry for any job. The single point fastening of mounts 20 provides for rapid attachment of the system 10 and for easy angular adjustment of a wall support 20 relative to an adjacent support 20. The present system 20 provides that accurately holding the mounting distance between wall supports 20 is not required since the supports 20 are separate loose pieces that are individually mounted. The present system 10 does not require a multiple-fastener mounting pattern (typical grab bars have 3 fasteners per end—6 total). Further the system 10 can be easily implemented with hex head fasteners and hex head fasteners can be installed with a drive socket rather than a screw driver. It's physically much easier to install a fastener with a ratchet socket wrench than a screwdriver. With hex head fasteners, much higher tightening torque can be achieved which results in greater holding force. Front mounting, rear mounting and back to back mounting configurations are all easily provided for without special tools or fasteners.

The system 10 provides a single versatile, product that's simple to install and the finished installation are esthetically pleasing. Further the system 10 provides for no exposed fasteners. The system 10 provides for unlimited lengths are possible by simply connecting bars together (appropriate couplers are shown in U.S. Pat. No. 9,181,709). The system 10 provides for significant reduction in installation labor with single point fastening. The system 10 provides for unrestricted mounting capabilities (horizontal, vertical, at any angle). The system 10 preferably utilizes stock rail members 12 cut to length and inexpensive standard fasteners instead of high cost specialty fasteners.

Figure 6:
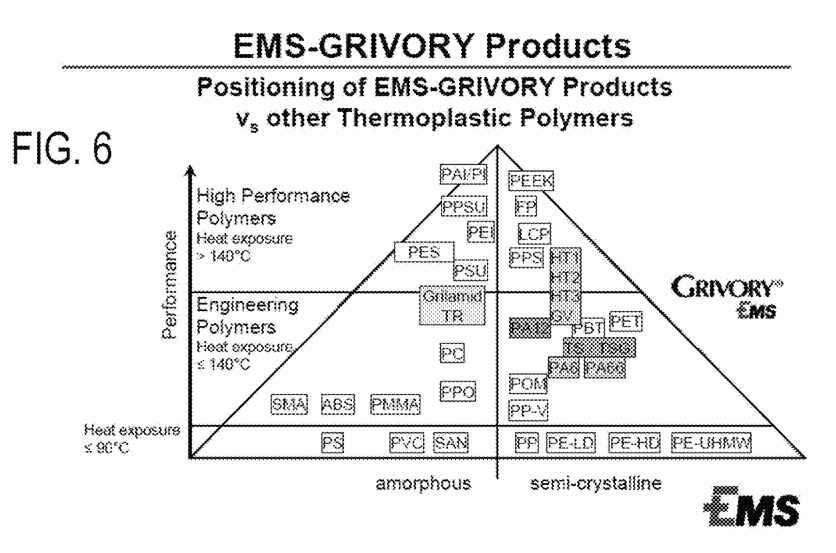
FIG. 6 illustrates a chart of the injection moldable metal replacement materials used in the one piece molded mount for the grab bar assembly of FIG. 1.

FIG. 6 illustrates the injection moldable metal replacement material used in the mounts 20. As discussed in further detail bellow grab bar 12 can be equipped with the following functionalities: Glow in the Dark grab bar; Lighted grab bar; Wireless speaker grab bar; Radio grab bar; Scent emitting grab bar; Heated grab bar and Vibrating grab bar. Where appropriate these integrated grab bar accessories can be actuated (switching on-off) by a number of different sensing technologies such as Motion-detecting (ultrasonic and microwave), Heat-sensing (infrared), Sound-sensing (acoustic), Touch sensing (capacitance and resistive), Light sensing (photocell), and Passive infrared sensing (occupancy). Mechanical switches can also be employed.

Figures 7, 8, 9, 10:
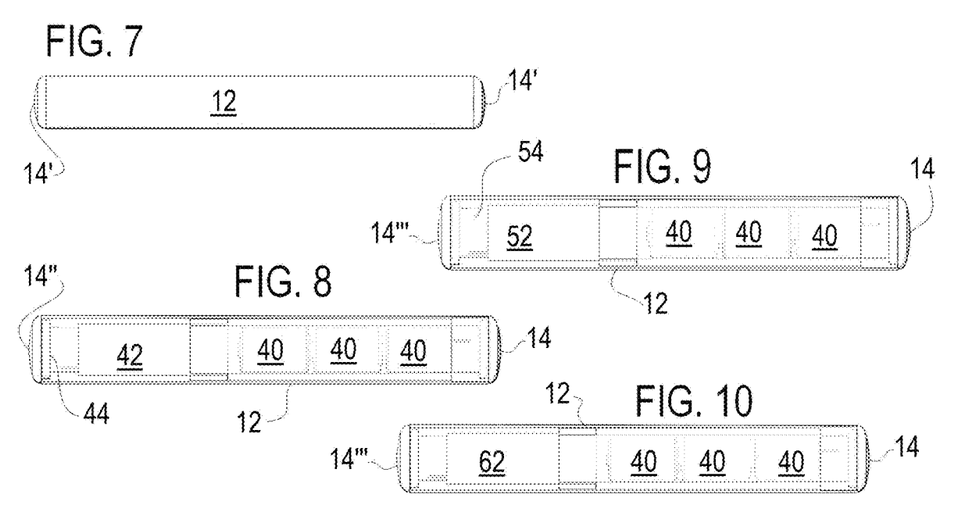
FIG. 7 schematically illustrates a glow in the dark grab bar for the grab bar assembly of FIG. 1.
FIG. 8 schematically illustrates a lighted grab bar for the grab bar assembly of FIG. 1.
FIG. 9 schematically illustrates a grab bar with integral speaker for the grab bar assembly of FIG. 1.
FIG. 10 schematically illustrates a grab bar with integral radio for the grab bar assembly of FIG. 1.

FIG. 7 demonstrates the aspects of the glow in the dark grab bar assembly 10. FIG. 7 illustrates the grab bar or rail member 12 with bar caps 14'. The mounts are not shown. Here the bar caps 14' can be made from glow in the dark material. It is also possible that the stock rail material 12 could be formed of glow in the dark material. Phosphorescence is the term for the process in which energy absorbed by a substance is released relatively slowly in the form of light. This is the proposed mechanism used for "glow-in-the-dark" materials forming the molded caps 14' (and possibly the bar 12) which are "charged" by exposure to light. Unlike the relatively swift reactions in fluorescence, such as those seen in a common fluorescent tube, phosphorescent materials "store" absorbed energy for a longer time, as the processes required to re-emit energy occur less often. For this phosphorescent-based purpose, strontium aluminate may be used as a coating pigment, or preferably as an additive to the plastic forming the molded caps 14' (or the bar 12). When added to the plastic, the strontium aluminate may be coated with a lubricant due to the hardness of the strontium aluminate particles. Other phosphorescent particles may be utilized. This construction provides illumination in dark conditions while eliminating the need for a powered light source. Additionally the molded mount caps 22 and the molded mounts 20 can be made from glow in the dark material.

FIG. 8—Lighted Grab bar assembly 10. The lighted grab bar 12 in this configuration is a device that will illuminate when activated by an external action such as touching the bar 12. Activation of the electronic aspects of the grab bar assemblies 10 of the present invention can be accomplished by any of the following known sensing methods/switches: Touch sensing of the rail 12 (via capacitance and resistive sensing), Motion-detecting (via ultrasonic or microwave sensors), Heat-sensing (via infrared sensors), Sound-sensing (acoustic sensors), Light sensing (photocell sensing—Note for the lighted grab bar the light sensing will turn on the lights 44 of the system 10 when sensing the light is below a given threshold rather than above), Passive infrared sensing (aka proximity or occupancy sensors), and Built in the bar switch i.e. tape switch or membrane switch. As the rail member 12 is a hollow tube with open ends, a device or mechanism with (or without a battery pack 40), etc. can be housed inside the bar 12. This is an advantage over current grab bars that have flanges that fasten to the wall. There is no convenient access to insert components and/or batteries into the grab bar.

The grab bar power source can be the battery pack 40 (i.e. series of batteries 40 in a carrier such as in a common flashlight), but it can also be external as in an cord which plugs into a common household receptacle. FIG. 8 illustrates the bar 12 portion of the grab bar assembly 10. Contained within the bar 12 are a circuit board with the appropriate circuitry shown at 42, batteries 40 and a light source 44 (such as LED's) adjacent at least one accommodating bar cap 14". The accommodating bar cap 14" will be formed to accommodate the LED light and will be formed as transparent or translucent member. The bar cap 14″ may include conventional light dispersion features/optics to better disperse the light. Any of the above sensing technologies can be used to activate and deactivate the light source 44 (LED's). Deactivation can also be accomplished by a timer circuit incorporated on the circuit board 42.

FIG. 9—Wireless Speaker Grab bar: The bar 12 of this embodiment houses an audio speaker 54 which can be utilized in conjunction with any wireless technology such as Bluetooth via controller 52. FIG. 9 illustrates the bar portion 12 of the Grab bar assembly 10. Contained within the bar 12 is a controller 52 including generally a circuit board and wireless receiver, batteries 40 and a sound source (speakers 54) adjacent a bar cap 14‴. The bar cap 14‴ is perforated to assist in the dissemination of sound. Any of the above sensing technologies can be used to activate and deactivate the sound source (speakers 54). Deactivation can also be accomplished by a timer circuit incorporated on the circuit board. The grab bar power source can also be external as in plugging into a common household receptacle.

FIG. 10—Radio Grab bar: The bar 12 of this embodiment houses a Radio 62. FIG. 10 illustrates the bar portion 12 of the grab bar assembly 10. Contained within the bar 12 is the radio 62 with (speakers not identified separately) adjacent a bar cap 14‴. Any of the above sensing technologies can be used to activate and deactivate the radio. Deactivation can also be accomplished by a timer circuit incorporated on the circuit board. The grab bar power source can also be external as in plugging into a common household receptacle. The radio components may be wirelessly coupled to an external controller to allow the user to adjust the radio (adjust the volume and change the radio station which is tuned in and change the format (e.g., AM, FM or Satellite). Alternatively controls may be provided or accessible through an access opening in the bar 12, but such a design requires a specific bar to be used or a separate opening cutting step to be used, such that wireless coupled controls are preferred.

Figure 11:
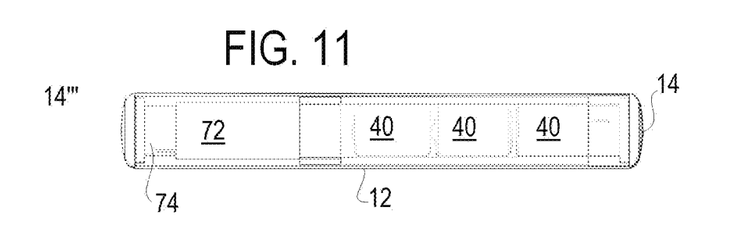
FIG. 11 schematically illustrates a grab bar with integral scent release unit for the grab bar assembly of FIG. 1.

FIG. 11—Scent Emitting Grab bar: This version provides the capability of emitting a pleasing scent into the environment (e.g., aroma therapy) while concealing the mechanism inside the bar 12. FIG. 11 illustrates the bar portion 12 of the Grab Bar assembly 10. The bar 12 can house a scent emitting device 72 similar to those found in GLADE PLUG IN® and FABREZE NOTICEABLES® brand air fresheners. Contained within the bar 12 is the scent emitting device 72 (often a heating unit), batteries 40 and the appropriate scent emitting material 74 (often a solid, semisolid or liquid in a container that cooperates with the device 72. A timer circuit incorporated on the circuit board or controller of the unit 72 can expel scent at adjustable intervals or continuously. The scent compound 74 can be replenished via the bar cap 14‴. The perforated bar cap 14‴ will assist in emitting and disseminating the scent. The grab bar power source can also be external as in plugging into a common household receptacle.

Not shown in FIG. 11 is a Solid Room Freshener type. The bar caps 14‴ can be configured to hold replaceable solid or semi-solid room air fresheners such as GLADE® Solid Air Freshener. No power source or circuit board is required for this type of scent emitting unit.

Figure 12:
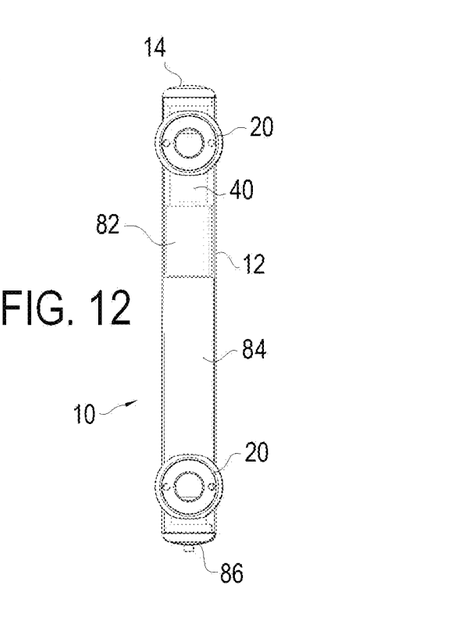
FIG. 12 schematically illustrates a grab bar assembly with integral powered liquid or powder dispenser according to the present invention.

FIG. 12 discloses a Battery Powered Liquid (or powder) Dispenser grab bar system 10 according to one aspect of the present invention wherein the system 10 will store and dispense a liquid (or powder) such as soap, body wash, lotion, hand cleaners etc. when activated by an external action such as touching the bar 12. Activation can be accomplished by any of the following sensing methods: Touch sensing, Motion-detecting, Passive infrared sensing, or a Built in the bar switch i.e. tape switch, membrane switch. The bar 12 of this embodiment can house the batteries 40 for powering the dispenser, a pump 82 for dispensing, and a liquid reservoir 74 (refillable via the top cap 14), and a modified lower bar cap 86 having a dispending nozzle therein controlled by pump 82. The system 10 is well suited for a bathtub to yield a safety grab bar system with integrated dispenser for soap, conditioner, body wash or the like. Hotels and health clubs represent users of this embodiment.

Figure 13:
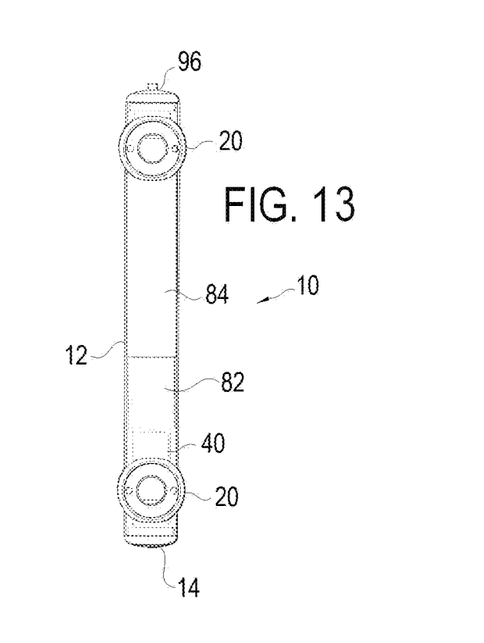
FIG. 13 schematically illustrates a grab bar assembly with integral liquid or powder spraying dispenser according to the present invention.

The embodiment of FIG. 13 is a Battery Powered Rotary Sprayer grab bar assembly 10. The embodiment is substantially an inverted version of the embodiment of FIG. 12 wherein the dispenser end cap 86 (now on the top of the assembly 10) is replaced formed in the form of a rotary or radial directed sprayer/end cap 96. The construction of spraying dispensing nozzles is known in the art and not described herein in detail. Essentially the device that will store and spray a liquid, such as a shower cleaner in a rotary pattern to clean the interior of a shower. It can be activated by any of the above methods, or from a remote controller. This embodiment, with remote control activation, is particularly useful for industry applications for cleaning showers (i.e. hotels, hospitals, health clubs and the like). When it is time to clean and disinfect the shower which incorporates the grab bar 10 the worker activates the sprayer (via remote or the like) and the system will automatically spray the shower or bath area. The worker can then typically wait an allotted time (for example, while cleaning the remainder of the room) and wipe down the shower/bath area after the prerequisite amount of time. It almost provides a self cleaning and disinfecting bath/shower area, and the system still provides a useful grab bar for safety applications by other users of the bath.

Figure 14:
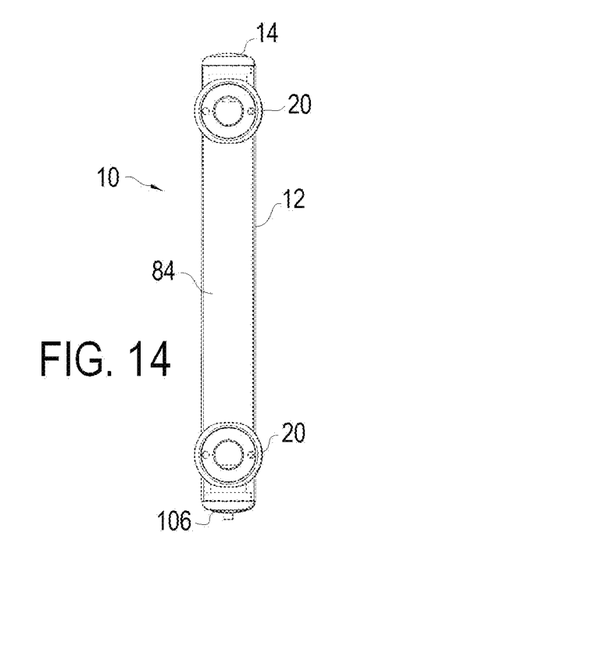
FIG. 14 schematically illustrates a grab bar assembly with integral powered liquid or powder dispenser according to the present invention.

FIG. 14 illustrates a Non-Powered Liquid/powder Dispenser grab bar assembly 10 according to the present invention in which the device will store and dispense a liquid or powder such as soap, body wash, lotion, hand cleaners etc. when activated by an external manual action such as moving a lever or depressing a plunger in the dispenser head/bar cap 106. The details of this type of dispenser are generally known in the art and not described in detail herein other than they are designed to fit into the rail member 12 as shown.

Another alternative is a heated grab bar, not shown, which provides the capability of heating the bar. In areas that are cold or wherever a warm hold is required, the bar can house an electric heater. It can be powered by battery or externally as in plugging into a common household receptacle. Another alternative integrated accessory is a Vibrating grab bar, not illustrated. This version provides the capability of vibrating the bar such as in a hand held massager. It would offer therapeutic benefits to the user.

It will be apparent to those of ordinary skill in the art that various modifications may be made to the present invention without departing from the spirit and scope thereof. The scope of the invention is not to be limited by the illustrative examples described above.

What is claimed is:

1. A rapidly mounted, modular, universal grab bar system: comprising:
  a plurality of wall mounted supports, wherein each wall mounted support is formed as a molded member having a wall end configured to be adjacent the wall with a central fastener opening extending from the wall end, wherein the molded member forming the wall mounted support includes a rail member recess formed as a through-hole extending from one side of the wall mounted support through to an opposed side of the wall mounted support and intersecting with the central fastener opening, wherein each wall mounted support is configured to be secured to a wall, and wherein the central fastener opening is formed as a first bore extending from the wall end to an enlarged head receiving portion having a diameter larger than a diameter of the first bore extending to the distal end, wherein the enlarged head receiving portion is accessible through the distal end of the wall support, wherein the intersection of the enlarged head receiving portion with the first bore is at least one half of the distance of from the wall end to the through-hole forming the rail member recess, and including an annular recess spaced from and surrounding the first bore of the central fastener opening and at least a portion of the enlarged head receiving portion of the central fastener opening, and wherein a thickness of the annular recess is less in the annular recess surrounding at least a portion of the enlarged head receiving portion than a thickness of the annular recess surrounding the first bore of the central fastener opening;

a plurality of central fasteners, each central fastener with a drive head and associated with at least one wall mounted support and received within the central fastener opening thereof for securing each wall mounted support to the wall through the central fastener, wherein the central fastener is configured to be accessed through the distal end of the wall mounted support, wherein the wall mounted support is, at least at one time, rotationally adjustable about the central fastener; and at least one stock rail member forming the handrail member, wherein each rail member is received within rail member recesses of the wall mounted supports extending entirely through the through-hole forming the rail member recess and wherein the central fastener extends perpendicular to the axis of the rail member, wherein the rail member recess of each wall mounted support being formed as a through-hole whereby the recess substantially encircles the rail member which is received within rail member recess and aligns the rail member which is received within rail member recess with the associated central fastener which is received within the central fastener opening.

2. The rapidly mounted, modular, universal grab bar system according to claim 1 wherein at least one component of the system is formed from phosphorescent material.

3. The rapidly mounted, modular, universal grab bar system according to claim 2 further including bar caps at each end of the rail member, wherein each bar cap is a molded member including strontium aluminate.

4. The rapidly mounted, modular, universal grab bar system according to claim 1 further including a light source within the rail member which is configures to illuminate when activated by an external action.

5. The rapidly mounted, modular, universal grab bar system according to claim 4 further including bar caps at each end of the rail member, wherein at least one bar cap is formed as a transparent or translucent member.

6. The rapidly mounted, modular, universal grab bar system according to claim 4 wherein the transparent or translucent bar cap includes light dispersion features.

7. The rapidly mounted, modular, universal grab bar system according to claim 1 further including an audio speaker housed within the rail member.

8. The rapidly mounted, modular, universal grab bar system according to claim 7 wherein the speaker is a wireless speaker.

9. The rapidly mounted, modular, universal grab bar system according to claim 7 further including bar caps at each end of the rail member, wherein at least one bar cap is perforated to assist in the dissemination of sound.

10. The rapidly mounted, modular, universal grab bar system according to claim 7 wherein the speaker is part of a radio unit housed within the rail member.

11. The rapidly mounted, modular, universal grab bar system according to claim 10 further including bar caps at each end of the rail member, wherein at least one bar cap is perforated to assist in the dissemination of sound.

12. The rapidly mounted, modular, universal grab bar system according to claim 10 wherein the radio unit is a wireless coupled to an external radio controller.

13. The rapidly mounted, modular, universal grab bar system according to claim 1 further including a scent emitting device housed within the rail member.

14. The rapidly mounted, modular, universal grab bar system according to claim 13 further including bar caps at each end of the rail member, wherein at least one bar cap is perforated to assist in the dissemination of scents.

15. The rapidly mounted, modular, universal grab bar system according to claim 14 wherein the scent emitting device housed within the rail member is powered by batteries housed within he rail member.

16. The rapidly mounted, modular, universal grab bar system according to claim 1 further including a liquid or powder housing and dispensing device housed within the rail member.

17. The rapidly mounted, modular, universal grab bar system according to claim 16 further including a lower bar cap on the rail member having a dispending nozzle coupled to the liquid or powder housing and dispensing device housed within the rail member.

18. The rapidly mounted, modular, universal grab bar system according to claim 16 further including an upper bar cap on the rail member having a spraying nozzle coupled to the liquid or powder housing and dispensing device housed within the rail member.

19. A rapidly mounted, modular, universal grab bar system: comprising:

a plurality of wall mounted supports, wherein each wall mounted support is formed as a one piece molded member having a wall end configured to be adjacent the wall with a central fastener opening extending from the wall end, wherein the one piece molded member forming the wall mounted support includes a rail member recess formed as a through-hole extending from one side of the wall mounted support through to an opposed side of the wall mounted support and intersecting with the central fastener opening, and including an annular recess spaced from and surrounding the central fastener opening, and wherein a thickness of the annular recess is greater in a portion of the annular recess adjacent the wall than a thickness of the annular recess spaced from the wall;

a plurality of central fasteners, each central fastener associated with at least one wall mounted support and received within the central fastener opening thereof for securing each wall mounted support to the wall through the central fastener;

a stock rail member forming the handrail member, wherein each rail member is received within rail member recesses of the wall mounted supports extending entirely through the through-hole forming the rail member recess; and bar caps at each end of the rail member, wherein at least one bar member is configured to facilitate the dissemination of light, sound, scent, liquids or solids there through.

20. The rapidly mounted, modular, universal grab bar system according to claim 19 further including a liquid or powder housing and dispensing device housed within the rail member.

\* \* \* \* \*